(12) United States Patent
Honcoop et al.

(10) Patent No.: US 11,160,698 B2
(45) Date of Patent: Nov. 2, 2021

(54) DIAPER BAND WITH CENTRAL INNER-FACING HOOK FABRIC AND SECURE REAR HOOK AND LOOP FABRIC CLOSURE

(71) Applicants: Justin L. Honcoop, Garfield, WA (US); Jessie N. Honcoop, Garfield, WA (US)

(72) Inventors: Justin L. Honcoop, Garfield, WA (US); Jessie N. Honcoop, Garfield, WA (US)

( * ) Notice: Subject to any disclaimer, the term of this patent is extended or adjusted under 35 U.S.C. 154(b) by 609 days.

(21) Appl. No.: 15/655,364

(22) Filed: Jul. 20, 2017

(65) Prior Publication Data

US 2019/0021915 A1    Jan. 24, 2019

(51) Int. Cl.
*A61F 13/64* (2006.01)
*A61F 13/49* (2006.01)
(Continued)

(52) U.S. Cl.
CPC .............. *A61F 13/64* (2013.01); *A61F 13/45* (2013.01); *A61F 13/49004* (2013.01);
(Continued)

(58) Field of Classification Search
CPC ...... A61F 13/56; A61F 13/5622; A61F 13/64; A61F 13/49004
See application file for complete search history.

(56) References Cited

U.S. PATENT DOCUMENTS

| 1,544,312 A | 6/1925 | Gray |
| 3,057,353 A | 10/1962 | Casale |

(Continued)

FOREIGN PATENT DOCUMENTS

| CA | 2101122 A1 | 3/1995 | |
| CN | 101466339 A * | 6/2009 | ............. A61F 13/56 |

(Continued)

OTHER PUBLICATIONS

Website Link: http://www.aliexpress.com/store/product/Free-shipping-pororo-baby-cotton-diaper-fixed-belt-velcro-stretchable-diaper-band/429618_1713262176.html Downloaded Aug. 4, 2016 Pororo baby cotton diaper fixed belt velcro stretchable diaper band.

(Continued)

*Primary Examiner* — Susan S Su

(74) *Attorney, Agent, or Firm* — Russ Weinzimmer & Associates, P.C.

(57) ABSTRACT

A diaper band for ensuring that a toddler cannot remove a diaper secured thereby. The diaper band has central inner-facing hook fabric that can be attached to the fabric on the front of a typical diaper (disposable or reusable). The diaper band also has ends bearing hook and loop material that are securable to the back of the diaper behind the back of the toddler, to ensure that the toddler cannot detach the diaper band. The diaper band securely covers the attachment tabs of the diaper, so that the toddler cannot undo the diaper tabs. The central inward-facing hook fabric can be one or more material patches that are big enough to grab onto the front fabric of the diaper, the same front fabric for attaching the diaper tabs. Alternatively, the central inward-facing hook material region can extend along the entire length of the diaper band.

11 Claims, 5 Drawing Sheets

(51) Int. Cl.
*A61F 13/62* (2006.01)
*A61F 13/56* (2006.01)
*A61F 13/45* (2006.01)
*A61F 13/00* (2006.01)

(52) U.S. Cl.
CPC ........ *A61F 13/49007* (2013.01); *A61F 13/56* (2013.01); *A61F 13/5622* (2013.01); *A61F 13/622* (2013.01); *A61F 13/00* (2013.01)

(56) References Cited

U.S. PATENT DOCUMENTS

| | | | |
|---|---|---|---|
| 3,561,446 A | 2/1971 | Jones, Sr. | |
| 3,653,381 A * | 4/1972 | Warnken | A61F 13/49004 |
| | | | 604/391 |
| 3,847,702 A | 11/1974 | Jones, Sr. | |
| 3,980,460 A | 9/1976 | Nelson et al. | |
| 4,402,690 A * | 9/1983 | Redfern | A61F 13/622 |
| | | | 604/385.25 |
| 4,813,949 A | 3/1989 | O'Rourke | |
| 5,135,522 A * | 8/1992 | Fahrenkrug | A61F 13/64 |
| | | | 604/385.3 |
| 5,137,526 A | 8/1992 | Coates | |
| 5,214,806 A * | 6/1993 | Flores | A41B 13/00 |
| | | | 2/300 |
| 5,242,436 A | 9/1993 | Weil et al. | |
| 5,374,262 A * | 12/1994 | Keuhn, Jr. | A61F 13/622 |
| | | | 604/391 |
| 5,386,595 A * | 2/1995 | Kuen | A61F 13/64 |
| | | | 2/400 |
| 5,445,628 A * | 8/1995 | Gipson | A61F 13/62 |
| | | | 604/392 |
| 5,722,127 A | 3/1998 | Coates | |
| 5,906,604 A * | 5/1999 | Ronnberg | A61F 13/64 |
| | | | 604/386 |
| 5,916,206 A * | 6/1999 | Otsubo | A61F 13/496 |
| | | | 604/385.27 |
| 6,342,050 B1 * | 1/2002 | Ronnberg | A61F 13/625 |
| | | | 604/392 |
| 6,413,249 B1 * | 7/2002 | Turi | A61F 13/49019 |
| | | | 604/387 |
| 6,443,930 B1 * | 9/2002 | Silverstein | A61F 13/471 |
| | | | 604/349 |
| 6,449,775 B1 | 9/2002 | Battaglia | |
| 7,264,686 B2 | 9/2007 | Thorson et al. | |
| 7,544,628 B2 * | 6/2009 | Stupperich | D04H 1/559 |
| | | | 442/327 |
| 8,029,488 B2 | 10/2011 | Ashton et al. | |
| 8,449,518 B2 * | 5/2013 | Allison-Rogers | A61F 13/15699 |
| | | | 604/374 |
| 9,211,220 B2 * | 12/2015 | Schambon | A61F 13/505 |
| 2002/0052584 A1 * | 5/2002 | Forgar | A61F 13/49015 |
| | | | 604/358 |
| 2002/0151858 A1 * | 10/2002 | Karami | A61F 13/49 |
| | | | 604/385.3 |
| 2003/0069557 A1 * | 4/2003 | Driskell | A61F 13/49011 |
| | | | 604/385.3 |
| 2004/0074450 A1 | 4/2004 | Soares et al. | |
| 2005/0143709 A1 * | 6/2005 | Lindstrom | A61F 13/5622 |
| | | | 604/391 |
| 2005/0192555 A1 * | 9/2005 | Thomas | A61F 13/64 |
| | | | 604/402 |
| 2006/0167432 A1 * | 7/2006 | Sigari | A61F 13/505 |
| | | | 604/391 |
| 2006/0167433 A1 * | 7/2006 | D'Alcini | A61F 13/5622 |
| | | | 604/392 |
| 2007/0066953 A1 * | 3/2007 | LaVon | A61F 13/5622 |
| | | | 604/392 |
| 2010/0036340 A1 * | 2/2010 | Allison-Rogers | A61F 13/15699 |
| | | | 604/367 |
| 2010/0179496 A1 * | 7/2010 | Roe | A61F 13/4752 |
| | | | 604/368 |
| 2011/0160690 A1 * | 6/2011 | Schoenbeck | A61F 13/49011 |
| | | | 604/385.16 |
| 2012/0003421 A1 * | 1/2012 | Sollmann | A61F 13/4902 |
| | | | 428/131 |
| 2014/0130236 A1 | 5/2014 | Mack | |
| 2014/0276524 A1 * | 9/2014 | Breeden | A61F 13/64 |
| | | | 604/389 |
| 2016/0279000 A1 * | 9/2016 | Bader | A61F 13/625 |

FOREIGN PATENT DOCUMENTS

| | | | | |
|---|---|---|---|---|
| CN | 203724329 U | | 7/2014 | |
| CN | 103816010 B | * | 1/2016 | ........ A61F 13/49011 |

OTHER PUBLICATIONS

Website Link: http://www.wholecheap.com/Sku/1244490/berenstain-cotton-leaf-fixed-with-diaper-with-diaper-diaper-diaper-buckle-fixation-band-regulation-size-baby-products Downloaded Aug. 4, 2016 Berenstain cotton leaf diaper buckle fixation band.
Website Link: http://www.mamabananasadventures.com/2015/02/moonmaker-cloth-diaper-review.html Downloaded Aug. 4, 2016 Mama Banana's Adventures: MoonMaker Cloth Diaper.
Website Link: https://www.youtube.com/watch?v=P4Uwnh6_L10 Downloaded Aug. 4, 2016 The GroVia Hybrid Diaper!
Website Link: https://www.youtube.com/watch?v=Djt2Fue95UA Downloaded Aug. 4, 2016 Boingo Cloth Diaper Fasteners vs. Snappi Diaper Fastener.

* cited by examiner

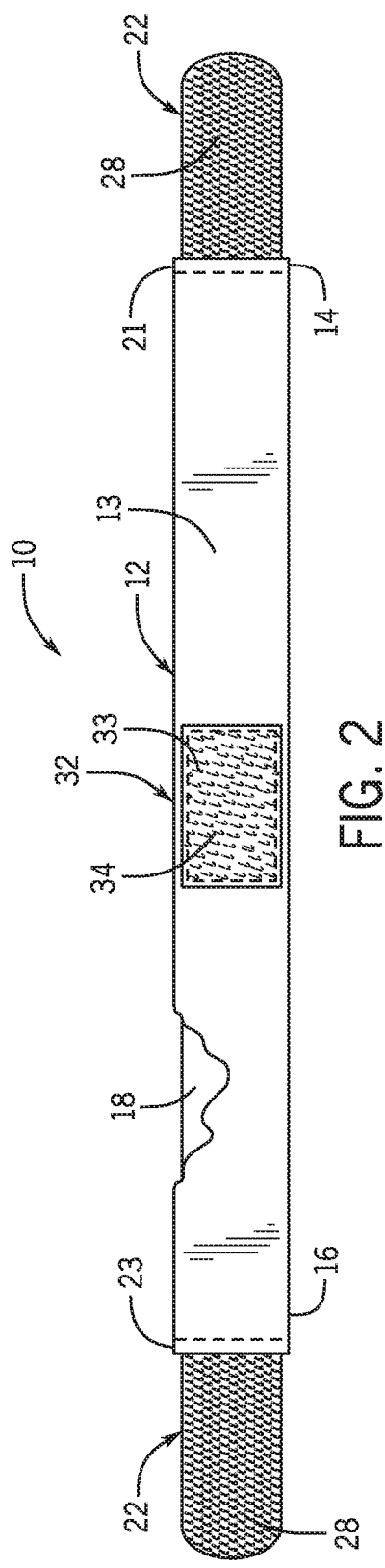
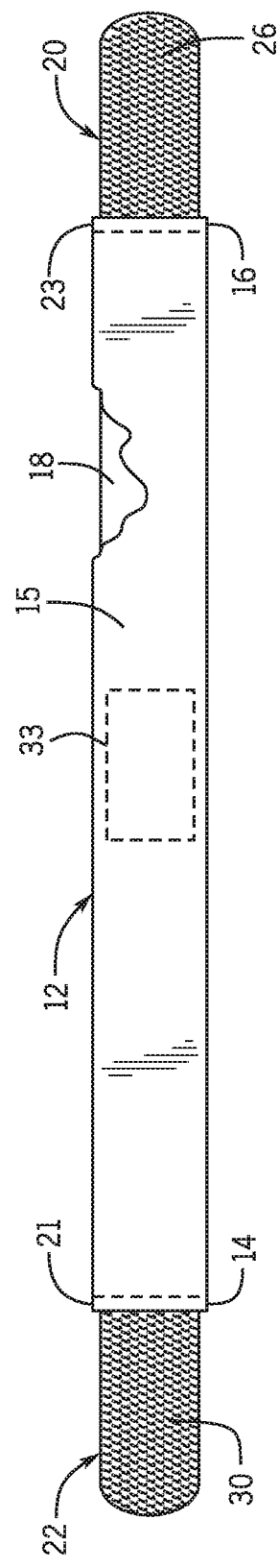

DIAPER BAND WITH CENTRAL INNER-FACING HOOK FABRIC AND SECURE REAR HOOK AND LOOP FABRIC CLOSURE

FIELD OF THE INVENTION

This invention relates generally to diapers, and particularly to devices for preventing removal of a diaper by a toddler wearing the diaper.

BACKGROUND OF THE INVENTION

Some toddlers between one and three years old begin to rebel against wearing a diaper, and learn to loosen and possibly remove their diaper, particularly at bed-time and during naps. Some parents observe that their child can detach one or both attachment tabs through their pajamas. It then becomes possible for the child to urinate and/or defecate inside the pajamas, which in turn can soil the bed sheets, blankets, and/or pillowcases.

This can transform into a full-blown rebellion, where the toddler starts ripping off the diaper, or refuses to wear a diaper entirely.

Some parents have tried putting on the pajamas backwards. This may prevent the toddler from unzipping or unsnapping them. However, this will not stop a determined toddler from reaching the diaper by puffing the waist of the pajamas away from the body to reach the diaper.

Some parents use duct tape, electrical tape, or medical tape to reinforce the sticky closure tabs on regular diapers so that the tabs cannot be opened. Attachment to the skin can cause rashes. Further, a determined and resourceful toddler can learn to peel off the additional tape. If the child cannot remove the tape, then it adheres so well that it must be cut off with scissors, resulting in injury to the toddler if the toddler is restless while the scissors are used.

Other parents place the child into a diaper, and then into pajama pants, and then into a sleep sack. The sleep sack adds one more layer that must be removed before the diaper can be removed. Even if the sleep sack is put on backwards, it can still be pulled down, thereby providing access to the diaper closures.

SUMMARY OF THE INVENTION

The diaper band solves the problem that many parents with young children in diapers struggle with. Some kids will somehow manage to get their diapers off, be it by taking their clothes off, or just by simply ripping the diaper tabs off through their clothing. The diaper band 10 of the invention is first centered and attached to the front of the diaper, and then each end of the diaper band 10 is wrapped around the sides of the diaper to the back side, adhering to the diaper material, as well as to the respective opposing end of the diaper band.

A general aspect of the invention is a diaper band for securing a diaper to a wearer. The diaper band includes: an inner elastic band having a right end and a left end; an outer elastic fabric cover extending along the inner elastic band from the right end to the left end; a right attachment strap, attached to the right end, the right attachment strap having an inward-facing side presenting hook material, and an outward-facing side presenting loop material; a left attachment strap, attached to the left end, the left attachment strap having an inward-facing side presenting hook material, and an outward-facing side presenting loop material; and a central attachment patch, attached to an inner portion of the outer elastic fabric cover, the central attachment patch inwardly presenting hook material configured to engage an outward-facing fabric surface of a diaper when the diaper band is worn to secure a diaper to the wearer.

In some embodiments, the central attachment patch is attached to central portion of the outer elastic fabric cover by sewing a seam through both sides of the outer elastic fabric cover.

In some embodiments, the outer elastic covering is made of a material that is thinner than the material of the inner elastic band.

In some embodiments, the outer elastic covering is bears a decorative pattern.

In some embodiments, the right attachment strap is attached to the right end of the inner elastic band by a sewed seam, and the left attachment strap is attached to the left end of the inner elastic band by a sewed seam.

In some embodiments, the central attachment patch extends to both the left attachment strap and the right attachment strap.

In some embodiments, the central attachment patch is three times as long as it is wide.

In some embodiments, the diaper band further includes: a second attachment patch to the left of the central attachment patch, and a third attachment patch to the right of the central attachment patch.

In some embodiments, the central attachment patch is divided into two detached half patches.

Another general aspect of the invention is a diaper band for securing a diaper to a wearer. This diaper band includes: an elastic band having an inner side, an outer side, a right end, and a left end; a right hook and loop extension having an inner side and an outer side, the right hook and loop extension being attached to the right end of the elastic band, the right hook and loop extension having hook material on the inner side and loop material on the outer side; a left hook and loop extension having an inner side and an outer side, the left hook and loop extension being attached to the left end of the elastic band, the left hook and loop extension having hook material on the inner side and loop material on the outer side; and a central hook-material portion attached to the inner side of the elastic band between the right end and the left end, the central hook-material portion being configured to engage with a respective loop-material area of an outer side of a front portion of the diaper.

In some embodiments, the diaper band further includes: an elastic fabric cover extending along the elastic band between the right end and the left end of the elastic band, the elastic fabric cover also including an inward-facing opening so as to expose a substantial portion of the central hook-material portion attached to the inner side of the elastic band.

In some embodiments, the central hook-material portion attached to the inner side of the elastic band between the right end and the left end extends over more than half of the distance between the right end and the left end.

In some embodiments, the elastic fabric cover is made of a material that is thinner than the material of the elastic band.

In some embodiments, the elastic fabric covering is bears a decorative pattern.

In some embodiments, the central hook-material portion is three times as long as it is wide.

Another general aspect of the invention is a diaper band for securing a diaper to a wearer, this diaper band including: an elastic band having an inner side, an outer side, a right end, and a left end; a right hook and loop extension having an inner side and an outer side, the right hook and loop extension being attached to the right end of the elastic band, the right hook and loop extension having hook material on the inner side and loop material on the outer side; a left hook and loop extension having an inner side and an outer side, the left hook and loop extension being attached to the left end of the elastic band, the left hook and loop extension having hook material on the inner side and loop material on the outer side; and an elastic fabric cover extending between the right end and the left end of the elastic band, the elastic fabric cover having at least one hook-material patch attached to a central portion of an inner side of the elastic fabric cover, the at least one hook-material patch being configured to engage with a respective loop-material area of an outer side of a front portion of the diaper.

In some embodiments, the at least one hook-material patch extends over more than half of the distance between the right end and the left end.

In some embodiments, the elastic fabric cover is made of a material that is thinner than the material of the elastic band.

In some embodiments, the elastic fabric covering is bears a decorative pattern.

In some embodiments, there are a plurality of hook-material patches between the right end and the left end.

BRIEF DESCRIPTION OF THE DRAWINGS

Many additional features and advantages will become apparent to those skilled in the art upon reading the following description, when considered in conjunction with the accompanying drawings, wherein:

FIG. 2 is an inner view of the diaper band of FIG. 1.

FIG. 3 is an outer view of the diaper band of FIG. 1.

DETAILED DESCRIPTION

Figure 1:
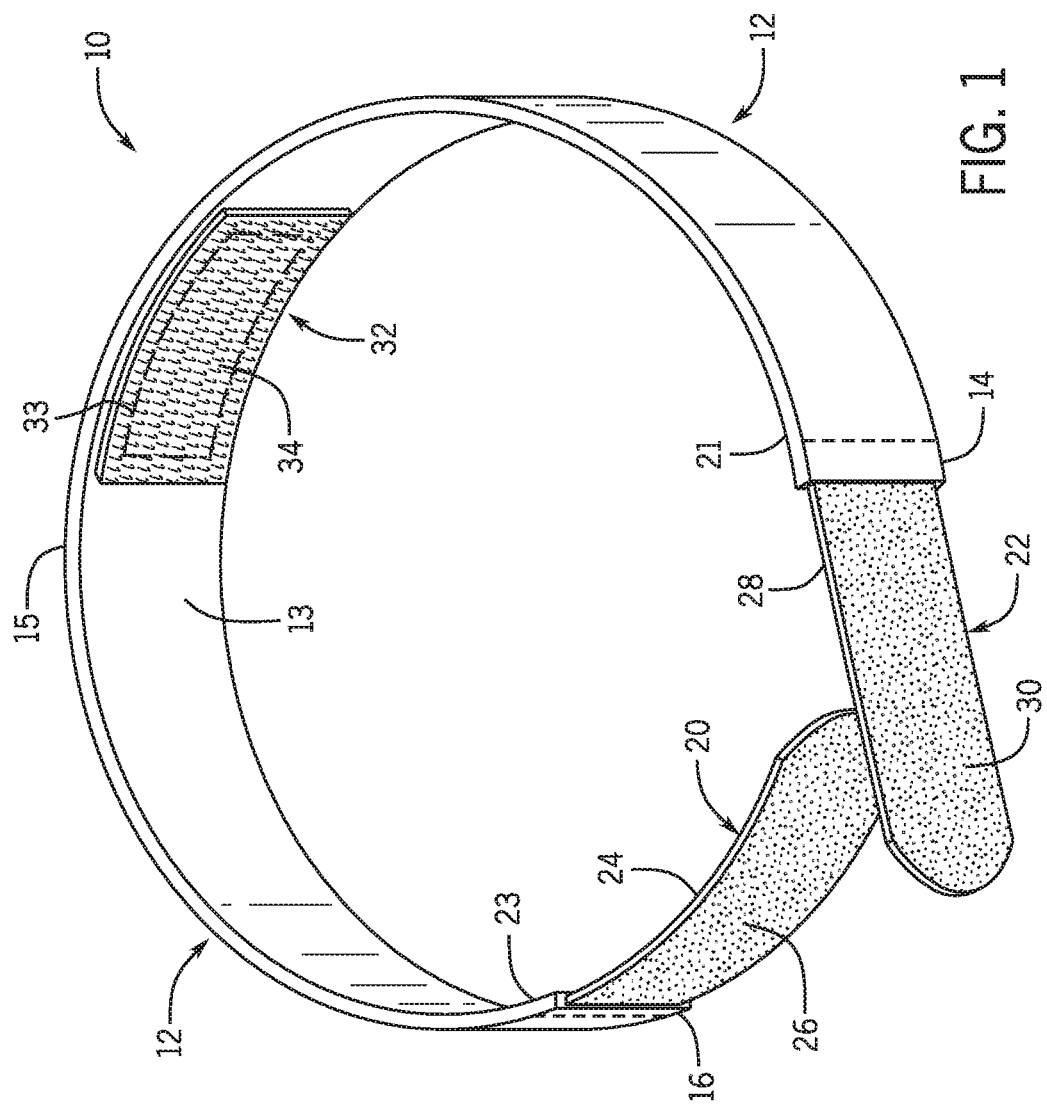
FIG. 1 is a perspective top rear view of an embodiment of the diaper band having a central attachment patch that is attached to a central portion of both the inner elastic band and both sides of the outer elastic fabric cover.

Referring to FIG. 1, the diaper band of the invention 10 includes an outer elastic fabric cover 12 having an inner surface 13, a right end 14, and a left end 16. An inner elastic band 18 (not visible in this view) runs inside the outer elastic fabric cover 12, extending inside the outer elastic fabric cover 12 from the right end 14 to the left end 16 of the outer elastic fabric cover 12.

A right attachment strap 20 is attached to the right end 14 via a seam 21, the right attachment strap 20 having an inward-facing side 24 (not visible in this view) presenting hook material, and an outward-facing side 26 presenting loop material.

A left attachment strap 22 is attached to the left end 16 via a seam 23, the left attachment strap 22 having an inward-facing side 28 (not visible in this view) presenting hook material, and an outward-facing side 30 presenting loop material.

A central attachment patch 32 is attached by a seam 33 to an inward-facing central portion 34 of the inner surface 13 of the outer elastic fabric cover 12, and to an outward-facing central portion of the outer surface 15 of the outer elastic fabric cover 12, and to the underlying respective portion of the inner elastic band 18. The central attachment patch 32 can be attached using a seam that runs at least around the periphery of the central attachment patch 32. Or, the central attachment patch 32 can be attached using a seam that runs at least along both the top edge and the bottom edge of the central attachment patch 32. Or, the central attachment patch 32 can be attached using a seam that runs at least along both the right edge and the left edge of the central attachment patch 32. Any other means of attachment that engages both sides of the outer elastic fabric cover 12 and the inner elastic band 18 can be used, such as an array, pattern, or sequence of plastic rivets. The central attachment patch 32 can also be attached to just inner surface 13 of the inward-facing central portion 34 of the outer elastic fabric cover 12 using fabric glue.

The central attachment patch 32 inwardly presents hook material that is configured to engage an outward-facing fabric surface (not visible in this view) of a diaper when the diaper band 10 is worn to secure the diaper to the wearer.

To attach around the diaper worn by a child, the diaper band 10 can be attached by securing the central attachment patch 32 to the outward-facing fabric surface on the front of the diaper. The right attachment strap 20 and the left attachment strap 22 are then pulled towards each other so as to overlap, and then are secured together by pressing the inward-facing hook material of the right attachment strap 20 into the outward-facing loop material of the left attachment strap 22. When the right attachment strap 20 and the left attachment strap 22 are secured together, they are secured over the attachment flaps of the diaper, thereby preventing the attachment flaps from being detached by the wearer of the diaper, which effectively prevents removal of the diaper by the wearer of the diaper.

FIG. 2 is an inner view of the diaper band 10 of FIG. 1, showing the central attachment patch 32, which is sewn using a seam 33 to the central portion 34 through both sides 13 and 15 of the outer elastic fabric cover 12, and through the underlying respective portion of the inner elastic band 18. The inner elastic band 18 runs through the outer elastic fabric cover 12. The left attachment strap 22 is sewn to the inner elastic band 18, and also preferably to the outer elastic fabric cover 12 via seam 23. Similarly, the right attachment strap 20 is sewn to the inner elastic band 18, and also preferably to the outer elastic fabric cover 12 via seam 21.

FIG. 3 is an outer view of the diaper band 10 of FIG. 1, showing the seam 33 that attaches the central attachment patch 32 to both sides of the outer elastic fabric cover 12, and to the underlying respective portion of the inner elastic band 18. The inner elastic band 18 runs through the outer elastic fabric cover 12. The left attachment strap 22 is sewn to the inner elastic band 18, and also preferably to the outer elastic fabric cover 12 via seam 23. Similarly, the right attachment strap 20 is sewn to the inner elastic band 18, and also preferably to the outer elastic fabric cover 12 via seam 21.

Figure 4:
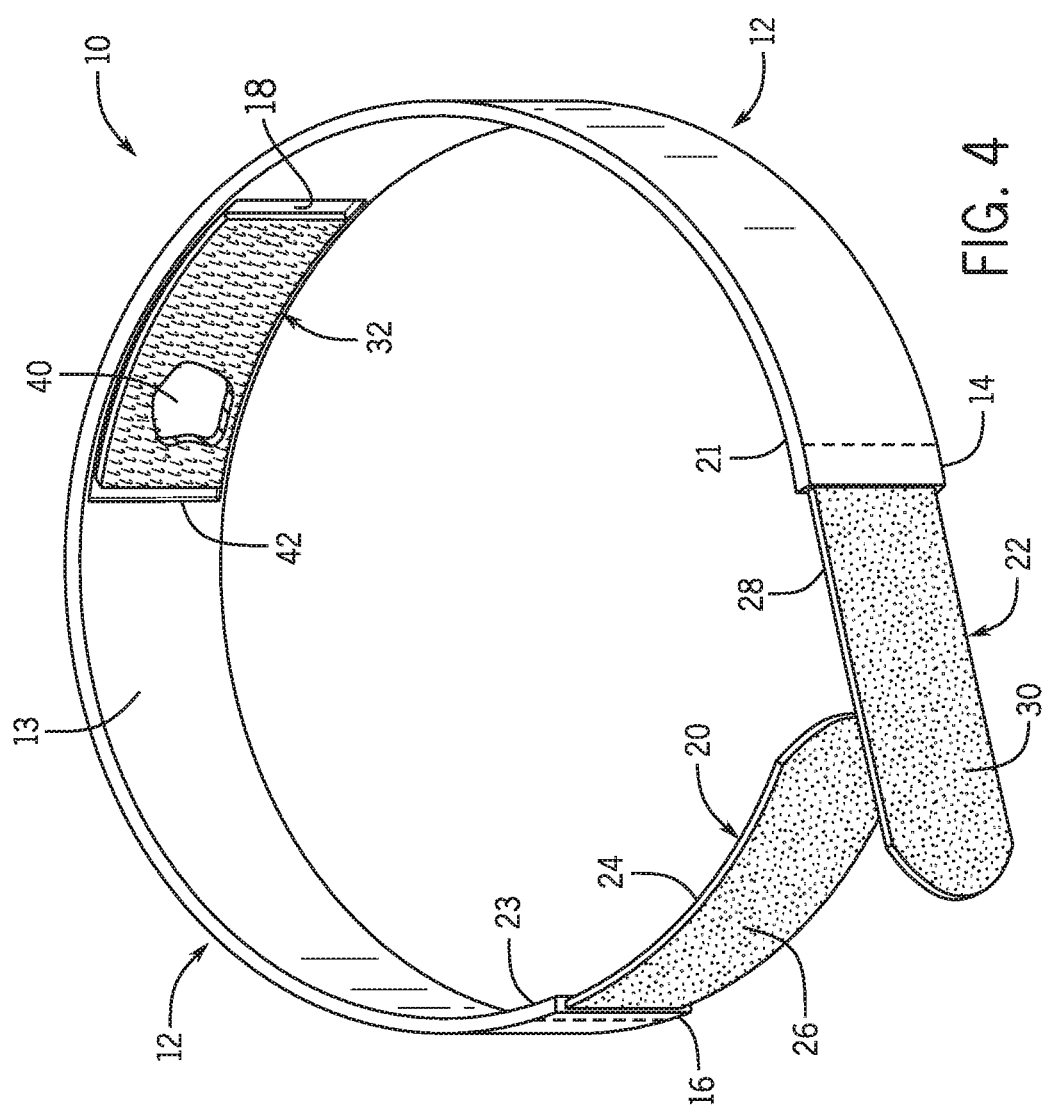
FIG. 4 is a perspective top rear view of an embodiment of the diaper band having a central attachment patch that is attached to a central portion of the inner elastic band, exposed by an inward-facing window in the outer elastic fabric cover.

Regarding FIG. 4, in an alternative embodiment, a central attachment patch 32 can be attached using an adhesive, for example, to an inward-facing central portion of the inner surface 40 of the inner elastic band 18. In this embodiment, a window 42 is cut out of the inner surface 13 of the outer elastic fabric cover 12 so as to expose the central attachment patch 32. The window 42 enables the hook material of the central attachment patch 32 to attach to the loop material of the front surface of the diaper.

Alternatively, the central attachment patch 32 could be attached to the inner elastic band 18 using a seam that runs at least around the periphery of the central attachment patch 32 to attach the central attachment patch 32 to the inner surface 40 of the inner elastic band 18.

Figure 5:
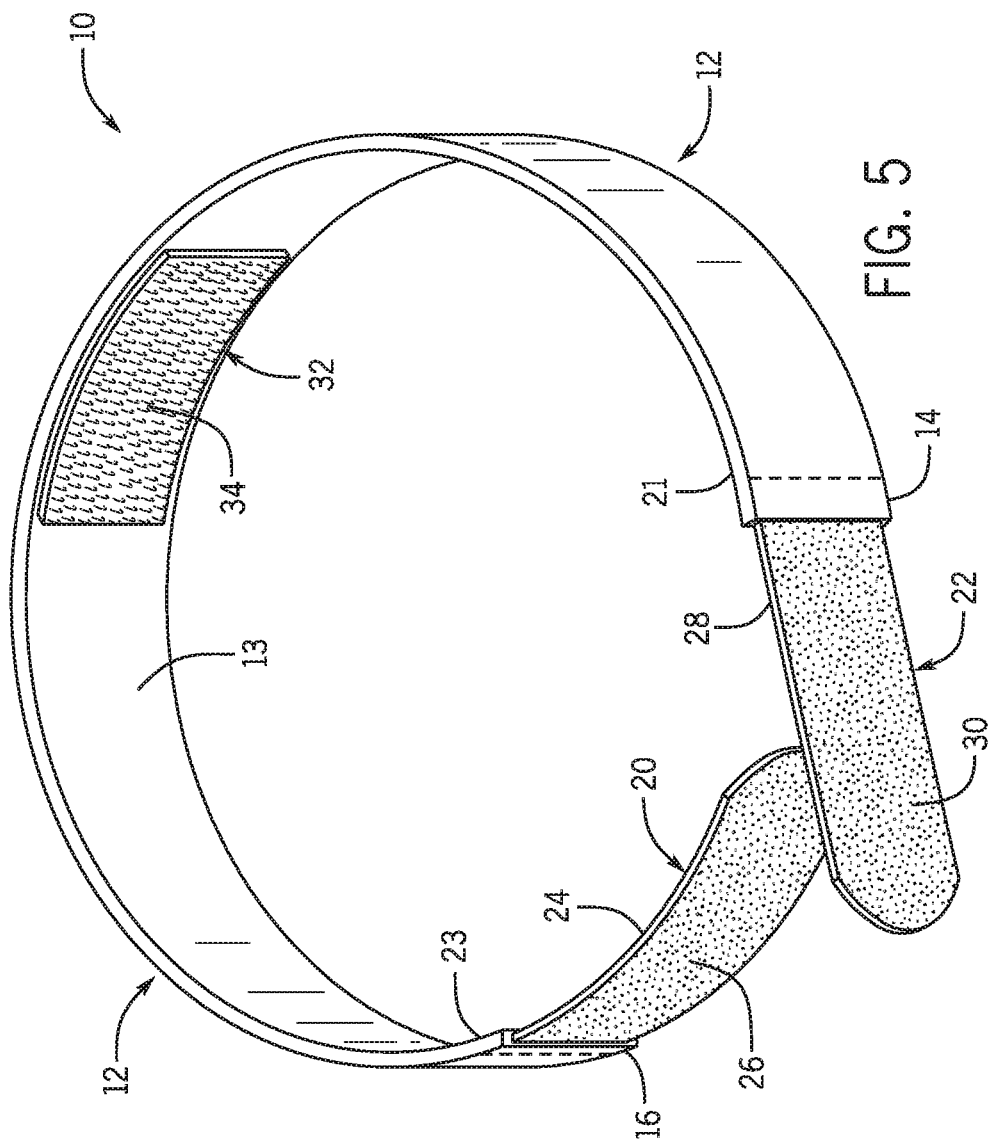
FIG. 5 is a perspective top rear view of an embodiment of the diaper band having at least one central attachment patch that is attached to a central portion of the inward-facing side of the outer elastic fabric cover.

Regarding FIG. 5, in another alternative embodiment, a central attachment patch 32 can be attached, using an adhesive, for example, only to an inward-facing central portion 34 of the inner surface 13 of the outer elastic fabric cover 12.

The central attachment patch 32 could also be attached only to an inward-facing central portion 34 of the inner surface 13 of the outer elastic fabric cover 12 using a seam that runs at least around the periphery of the central attachment patch 32.

Regarding the embodiments of FIGS. 1-5, the best material for the outer elastic fabric cover 12 is a nylon/elastic blend, because it has the same elastic stretch as the inner elastic band 18. Other fabrics can be used for the outer elastic fabric cover 12: 100% cotton, cotton blends, 100% Polyester, Polyester blends, or a 90%/10% Nylon/elastic blend.

The optimal width of the inner elastic band 18 is 1.75". This is slightly smaller in width than the attachment tabs of the diaper, and is wide enough to prevent it from rolling up. It is also possible to use a width from 1" to 2.5". The narrower band tends to roll more, making it more difficult for an adult to remove the band, since he/she must unroll the diaper. The wider 2.5" band works well, but can cause marks on the skin of the toddler, since it extends above and below the natural edges of the diaper it secures.

Regarding the thickness of the inner elastic band 18, the useful range of thickness is between 1.5 mm and 2 mm. This range of thickness provides just enough resistance to be difficult for the toddler to pull/grab/twist, yet not to be able to remove the band or the tabs of the diaper itself. Thinner material, such as material that is approximately 0.5 millimeters thick, can be too elastic, and can be stretched to 100% of its length with minimal force, thereby allowing a toddler to remove the diaper by sliding the elastic band 18 off of the diaper. Thicker material, such as material that is approximately 3 millimeters thick, can be too difficult to stretch, and although it would be excellent at diaper retention, it would be too rigid and uncomfortable for the toddler because it would impede movement.

The diaper band 10 having an inner elastic band 18 with a thickness of between 1.5 mm and 2 mm offers the right resistance to keep the child from being able to remove the diaper band 10, while being easy to put on and remove by the person changing the diaper.

The diaper band 10 is made of all washable materials, and it can have many color/design options for the outer elastic fabric cover 12.

The diaper band 10 is very easy to apply and remove for the parent/caregiver, but is hard to remove by the toddler/wearer, because the diaper band closure (the right attachment strap 20 and the left attachment strap 22 which can be secured together) is secured at the child's back where it is hard for the child to reach.

The diaper band 10 can be comfortably worn all day to prevent a toddler from removing his/her diaper. Testing has shown that toddlers were unable to remove the band 10, and ultimately ended up growing out of the phase of wanting to remove their diapers.

Figure 6:
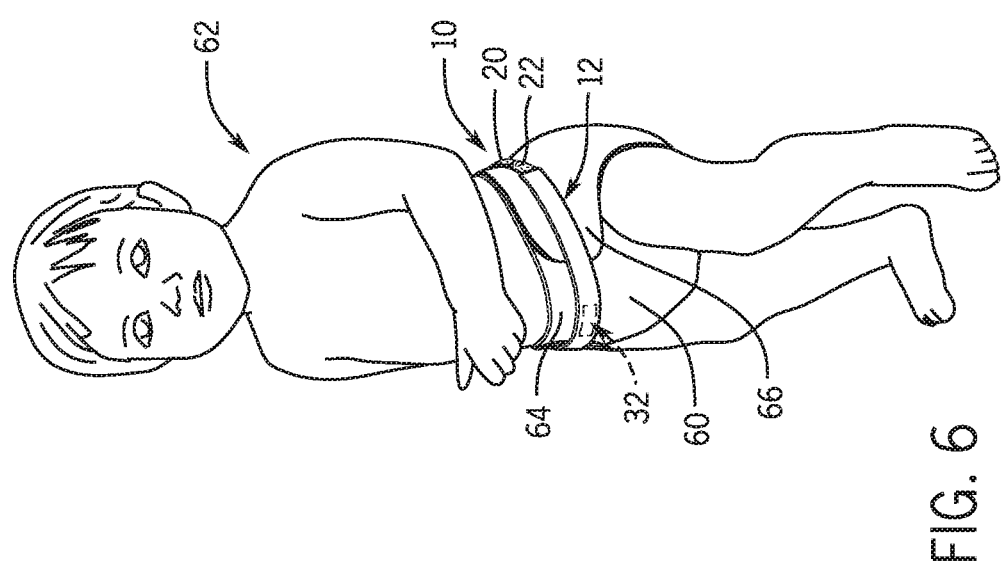
FIG. 6 is a perspective view of a toddler wearing the diaper band of FIG. 1, 4, or 5.

With reference to FIG. 6, to use the diaper band 10, first put the diaper 60 on the toddler 62 as usual. Then, take the diaper band 10 and press the central inner-facing hook-material portion 32 of the diaper band 10 onto the front center fabric portion 64 of the band of the diaper 60. Then, slide your hand with band 10 around the diaper 60 on each side, and affix one end 20 to the back of diaper 60, then affix the other end 22 to the back of diaper 60, and to the top of the end 20. Ends 20 and 22 will adhere to both the diaper 60, and to the opposing end, thereby making the diaper band 10 like a belt that covers the tabs 66 of the diaper 60, and thereby blocks access to the diaper tabs 66, and so prevents the child from detaching the diaper tabs 66. Since detaching the diaper tabs 66 is the first step to removing the diaper 60, the diaper 60 cannot be removed by the toddler without first detaching the ends 20 and 22 of the diaper band 10. Also, since the ends 20 and 22 of the diaper band 10 are attached BEHIND the back of the toddler, the ends 20 and 22 of the diaper band 10 are also not accessible to the toddler's hands. Therefore, the diaper band cannot be removed by the toddler 62. Thus, the diaper band 10 prevents removal of the diaper by the toddler 62.

The central inward-facing hook material region 32 can be just a patch that is long enough and wide enough to grab onto the front fabric 64 of the diaper 60, the same front fabric 64 to which the diaper tabs 66 attach. Alternatively, the central inward-facing hook material region 32 can extend along the entire length of the diaper band, ensuring that there will be some portion thereof that will attach to any fabric along the top outer circumference of the diaper 60. Thus, a continuous strip of hook material 32 can extend end-to-end, or can extend part of the way towards and symmetrically from the center of the front of the diaper 60 to each end 20 and 22.

Thus, the diaper band 10 can be used to secure a diaper 60 by first attaching a central portion 32 of hook material (such as VELCRO® brand hook material) of the diaper band 10 to the front of the diaper 60, and then each end 20 and 22 can be wrapped around the sides of the diaper 60, over the diaper tabs 66, and to the back of the diaper 60. Then, the ends 20 and 22 are pressed onto the diaper 60 so as to adhere to the diaper material 64, as well as onto one of the ends 20 and 22 of the band 10.

Other modifications and implementations will occur to those skilled in the art without departing from the spirit and the scope of the invention as claimed. Accordingly, the above description is not intended to limit the invention, except as indicated in the following claims.

What is claimed is:

1. A diaper band for impeding removal of a diaper by a wearer, the diaper including tabs that secure the diaper to the wearer, the diaper band comprising:
   an inner elastic band having a right end and a left end;
   an outer elastic fabric cover that covers the inner elastic band from the right end to the left end;
   a right attachment strap, attached to the right end, the right attachment strap having an inward-facing side presenting hook material, and an outward facing side presenting loop material;
   a left attachment strap, attached to the left end, the left attachment strap having an inward-facing side presenting hook material, and an outward-facing side presenting loop material; and
   a central attachment patch, attached to an inner portion of the outer elastic fabric cover, the central attachment patch presenting hook material configured to attach to a first outward-facing fabric surface of the diaper, wherein when the hook material of the central attachment patch is attached to the first outward facing fabric portion of the diaper:
the right and left attachment straps are configured such that the hook material of the first one of the right and left attachment straps can be attached to a second outward facing fabric portion of the diaper that is located on the diaper opposite from the first outward facing fabric portion, and
the hook material of the second one of the right and left attachment straps is configured to be attached to at least a portion of the loop material of the first one of the right and left attachment straps and at least a portion of the second outward facing fabric portion of the diaper, and
wherein when the first outward facing fabric portion is located at the front of the diaper and the central attachment patch is attached thereto, the right and left attachment straps are configured to be attached to the second outward facing fabric portion at the rear of the diaper, so that the tabs are substantially covered by the elastic fabric cover and the attached right and left attachment straps are functionally inaccessible to the wearer.

2. The diaper band of claim 1, wherein the central attachment patch is attached to the central portion of the outer elastic fabric cover by sewing a seam through both sides of the outer elastic fabric cover.

3. The diaper band of claim 1, wherein the outer elastic fabric covering is made of a material that is thinner than the material of the inner elastic band.

4. The diaper band of claim 1, wherein the right attachment strap is attached to the right end of the inner elastic band by a sewed seam, and the left attachment strap is attached to the left end of the inner elastic band by a sewed seam.

5. The diaper band of claim 1, wherein the central attachment patch extends to both the left attachment strap and the right attachment strap.

6. The diaper band of claim 1, wherein the inner elastic band is between approximately 1.5 mm and 1.75 mm thick.

7. The diaper band of claim 1, further comprising:
a second attachment patch to the left of the central attachment patch, and
a third attachment patch to the right of the central attachment patch.

8. The diaper band of claim 1, wherein the inner elastic band is between approximately 1.5 inches and 2 inches wide.

9. A diaper band for impeding removal of a diaper by a wearer of the diaper, the diaper including tabs that secure the diaper to the child, the diaper band comprising:
an elastic band having an inner side, an outer side, a right end, and a left end;
a right hook and loop extension having an inner side and an outer side, the right hook and loop extension being attached to the right end of the elastic band, the right hook and loop extension having hook material on the inner side and loop material on the outer side;
a left hook and loop extension having an inner side and an outer side, the left hook and loop extension being attached to the left end of the elastic band, the left hook and loop extension having hook material on the inner side and loop material on the outer side;
a central hook material portion attached to the inner side of the elastic band between the right end and the left end, the central hook material portion being configured to be attached to a first loop material area of the diaper; and
an elastic fabric cover that covers the elastic band between the right end and the left end of the elastic band, the elastic fabric cover also including an inward-facing opening so as to expose a substantial portion of the central hook material portion attached to the inner side of the elastic band,
wherein when the central hook material portion is attached to the first loop material area of the diaper:
the right and left hook and loop extensions are configured such that the hook material of a first one of the right and left hook and loop extensions can be attached to a second loop material area of the diaper that is located on the diaper opposite from the first loop material area, and
the hook material of a second one of the right and left hook and loop extensions is configured to be attached to at least a portion of the loop material of the first one of the right and left hook and loop extensions, and at least a portion of the second loop material area of the diaper,
wherein the elastic band is between approximately 1.5 inches and 2 inches wide, and
wherein when the first loop material area is located at the front of the diaper and is attached to the central hook material portion, the right and left hook and loop extensions are configured to be attached to the second loop material area of the diaper located at the rear of the diaper, so that the tabs are substantially covered by the elastic fabric cover and the attached right and left hook and loop extensions are functionally inaccessible to the wearer.

10. The diaper band of claim 9, wherein the central hook-material portion attached to the inner side of the elastic band between the right end and the left end extends over more than half of the distance between the right end and the left end.

11. The diaper band of claim 9, wherein the inner elastic band is between approximately 1.5 mm and 1.75 mm thick.

* * * * *